(12) United States Patent
Callery (10) Patent No.: US 11,207,101 B2
(45) Date of Patent: Dec. 28, 2021

(54) SYSTEM AND METHODS FOR FACILITATING CHILD BIRTH

(71) Applicant: UNIVERSITY OF MASSACHUSETTS, Boston, MA (US)

(72) Inventor: Ryan James Callery, Cambridge, MA (US)

(73) Assignee: University of Massachusetts, Boston, MA (US)

( * ) Notice: Subject to any disclaimer, the term of this patent is extended or adjusted under 35 U.S.C. 154(b) by 335 days.

(21) Appl. No.: 16/349,737

(22) PCT Filed: Nov. 15, 2017

(86) PCT No.: PCT/US2017/061777
§ 371 (c)(1),
(2) Date: May 14, 2019

(87) PCT Pub. No.: WO2018/093883
PCT Pub. Date: May 24, 2018

(65) Prior Publication Data
US 2020/0069332 A1    Mar. 5, 2020

Related U.S. Application Data (60) Provisional application No. 62/422,150, filed on Nov. 15, 2016.

(51) Int. Cl.
*A61B 17/42* (2006.01)
*A61M 29/02* (2006.01)
*A61B 17/00* (2006.01)

(52) U.S. Cl.
CPC .............. *A61B 17/42* (2013.01); *A61M 29/02* (2013.01); *A61B 2017/00438* (2013.01); *A61B 2017/4225* (2013.01)

(58) Field of Classification Search
CPC .......... A61B 17/42; A61B 2017/00438; A61B 2017/00557; A61B 2017/4225; A61M 25/1002; A61M 29/02
See application file for complete search history.

(56) References Cited

U.S. PATENT DOCUMENTS 5,582,620 A * 12/1996 Hirsch ................. A61B 42/10
606/192
2005/0055043 A1    3/2005 Foltz et al.
(Continued)

FOREIGN PATENT DOCUMENTS

EP    2896377 A1    7/2015
GB    2484105        4/2012
(Continued)

OTHER PUBLICATIONS

International Search Report issued in International Application No. PCT/US2017/061777, entitled "System and Methods for Facilitating Child Birth," dated Jan. 23, 2018.
(Continued)

*Primary Examiner* — Mohamed G Gabr
(74) *Attorney, Agent, or Firm* — Hamilton, Brook, Smith & Reynolds, P.C.

(57) ABSTRACT

The invention includes systems and methods using certain embodiments of a medical device to facilitate child birth through cervical ripening. Certain embodiments of the invention may include an elongated body having a proximal end and a distal end where the distal end terminates in a tip. The tip may be covered by a balloon disposed adjacent to the tip, and an expandable member may be positioned adjacent to the balloon such that when expanded, the expandable member may at least partially cover the balloon, and accommodate the user's finger to guide and place the device through the cervix and into the internal os, where, upon
(Continued)

expansion of the balloon, pressure is applied to the internal os to facilitate cervical ripening and child birth.

19 Claims, 7 Drawing Sheets

(56) References Cited

U.S. PATENT DOCUMENTS

| | | |
|---|---|---|
| 2008/0132908 A1 | 6/2008 | Nguyen |
| 2016/0000464 A1 | 1/2016 | Coomarasamy et al. |

FOREIGN PATENT DOCUMENTS

| | | | | |
|---|---|---|---|---|
| GB | 2484105 A | * | 4/2012 | ............... A61D 1/08 |
| WO | 01/68181 A1 | | 9/2001 | |

OTHER PUBLICATIONS

Written Opinion of the International Searching Authority issued in International Application No. PCT/US2017/061777, entitled "System and Methods for Facilitating Child Birth," dated Jan. 23, 2018.
International Preliminary Report on Patentability issued in International Application No. PCT/US2017/061777, entitled "System and Methods for Facilitating Child Birth," date of issuance May 21, 2019.
Extended European Search Report for EP Application No. 17872703.8, entitled "System and Methods for Facilitating Child Birth," dated Aug. 26, 2020.

\* cited by examiner

SYSTEM AND METHODS FOR FACILITATING CHILD BIRTH

CROSS REFERENCE TO RELATED PATENTS

This application claims the benefit of U.S. Provisional Patent Application No. 62/422,150 filed Nov. 15, 2016, which is incorporated by reference.

FIELD OF INVENTION

The field of invention relates generally to a medical system and methods used to dilate, or promote dilation of the cervical opening to facilitate child birth.

BACKGROUND OF THE INVENTION

Parturition—the process of child birth—requires the passage of the fetus from the uterus, through the cervix, and, finally, expulsion from the vagina. During the initial stages of parturition, dilation of the cervix—which includes the cervical canal, an internal os—which is the opening between the uterus and the cervical canal—and an external os—which is the opening between the cervical canal and the vagina—is accompanied by descent of the fetal head through the cervical canal.

Dilation of the cervix requires the softening of the connective tissue of the cervix, so that the cervix may stretch sufficiently to allow passage of the fetus into the vagina. This softening of the cervix is known as "cervical ripening". Initiation of the cervical ripening process may be characterized by the presence of certain critical factors including the release of enzymes, hormonal factors, and local pressure on the internal os as a result of the fetus' head during descent. However, sometimes the progression of cervical ripening is slow or is not naturally initiated, thus stalling the descent of the fetal head at the internal os. In such cases, cervical ripening may be stimulated through mechanical means—such as by the insertion and inflation of an instrument through the cervical canal to place pressure on the internal os—and/or by biochemical means—such as through the application of a medication (e.g. prostaglandins)—to increase, for example, collagen degradation of the cervix.

Mechanical means of stimulating cervical ripening are among the oldest known approaches to affect dilation of the cervix. Mechanical means are considered to provide several advantages over medications, including a lower risk of tachsystole/fetal distress and lower systemic side effects, plus may be a safer procedure for patients who have previously undergone a Caesarean section.

One mechanical means currently in use for the stimulation of cervical ripening is the Foley catheter. In one known procedure, the Foley catheter—which was originally designed as a urinary catheter—is inserted past the internal os and inflated to 50 to 80 ml with saline solution. The resulting inflated balloon is often 5 cm to 6 cm in diameter, and the area in contact with the internal os is roughly 30 to 45 $cm^2$. It has been found that the resultant pressure of the inflated balloon at the distal end of the Foley catheter in contact with the internal os may promote the ripening process.

Despite its widespread use, several disadvantages are associated with the Foley catheter. First, the catheter tip and balloon may deeply protrude into the uterus so that unwanted elevated pressure is applied to the head of the fetus. Moreover, the tip of the Foley catheter—extending into the uterus—may contact the head of the fetus.

Further, practitioners often find it difficult to place the Foley catheter into and through the cervical canal. To assist in the placement of the Foley-type catheter, an additional component—a rigid or—semi-rigid guidewire known as a stylet—is used. The use of such a multi-component system—catheter, balloon, stylet—may be cumbersome.

Lastly, the Foley catheter's original design and use was as a urinary catheter meant to be inserted into, and drain the bladder. Accordingly, the Foley catheter's design includes a large drainage channel. The resultant greater circumference of the catheter necessary to accommodate the large drainage channel may lead to further discomfort to the patient upon insertion into the cervix.

Accordingly, there is a need for a new cervical ripening system and methods that utilizes a device that does not apply unwanted pressure or contact the head of the fetus, causes less discomfort to the patient, and may be more easily positioned in the cervix to stimulate cervical ripening. The present invention satisfies this need.

SUMMARY OF THE INVENTION

The present invention is directed to a system and methods that use a cervical ripening device to facilitate child birth. Certain preferred embodiments of the system include a device which may be more easily positioned and inserted through the cervix to exert pressure on the internal os to facilitate the cervical ripening.

Certain embodiments of the device generally comprise an elongated body having a proximal end and a distal end, and at least one lumen disposed within the elongated body. The distal end of the elongated body may terminate in a tip. A balloon may be disposed at, or directly adjacent to the tip. Certain preferred embodiment of the device may also comprise an expandable member positioned adjacent to the balloon that, when expanded, may accommodate a physician's finger, thereby allowing tactile manipulation of the distal end of the device to facilitate the proper placement of the device through the cervical canal during the ripening procedure.

In further embodiments of the invention, the elongated body of the device may be constructed of a flexible, biocompatible material such as an elastomeric polymer, silicone, or silicon rubber. The elongated body may further include at least one internal lumen, through which fluids may be injected from an injection port, and/or removed from an opening or inlet at a proximal end of the elongated body.

Certain embodiments of the elongated body are sized and shaped to be minimally invasive, while still allowing a user to easily manipulate the device as needed. Preferably, the diameter of the elongated body may be about 2.5 mm to about 3 mm. In other embodiments, the length of the elongated body may be about 10 cm to about 40 cm. In other embodiments, the elongated body may be about 30 cm to about 40 cm in length. In still further embodiments, the length of the elongated body may be less than 10 cm.

In other preferred embodiments, the device may include at least one balloon disposed at or adjacent to the tip located at the distal end of the elongated body. Preferably, the balloon may be disposed at or within 5 mm of the tip so that only the minimal length of the device need be inserted through the cervical canal to the internal os. The balloon may be of any shape, including, but not limited to, spherical or oblong, and may include a single or multi-chamber design. The balloon may be sized and shaped such that it may be filled with about 60 cc to 80 cc of fluid, and preferably about 75 cc to apply optimal pressure to the internal os to facilitate ripening In preferred embodiments of the invention, the expandable member may be at least partially attached to the elongated body and may at least partially cover the balloon and tip. More preferably, the expandable member completely covers the balloon and tip and, after the balloon is expanded, may act as an outer layer of the balloon during placement in the cervical opening.

One preferred embodiment of a method for promoting cervical ripening comprises the steps of inserting at least a portion of an embodiment of a device of the invention through the cervical canal and into the internal os. Initially, the balloon and expandable member may be in an unexpanded state. The user may place a finger into the expandable member housing the balloon—the expandable member positioning the balloon tightly against the finger—thereby allowing the balloon and finger to move in conjunction during the procedure. Once the finger passes the cervix, the balloon may be slowly expanded in the internal os, and the finger may be simultaneously removed from the expandable member. The cervix may then hold the balloon and expandable member in place after removal of the finger to promote cervical ripening.

Among the advantages of the present invention are the following. Many devices currently used to facilitate ripening were originally designed for use as bladder catheters. These catheters include a large internal drain lumen and, as a result, have a relatively large overall diameter. The use of such a large device often causes discomfort to the patient during and after insertion. In comparison, the present inventive system includes a device having an elongated body without a drainage lumen. As a result, the overall diameter of the device may be very small and therefore may cause less discomfort to the patient during the procedure.

Another advantage of the present invention is being configured to facilitate the easy placement of the device into the cervical opening. Known devices often require a stylet, or other type of guide rod to achieve proper placement in the cervical opening. However, such extra components make these devices cumbersome to use and often result in inefficient placement of the device, incorrect placement of the device, and/or, because of the prolonged manipulation of the device, discomfort to the patient. In contrast, the system and methods according to the present invention use a device that includes an expandable member or expandable cup that may accommodate the physician's finger, and thereby allows the physician to quickly assess, through direct touch, the position of the device relative to the cervical opening with the finger, and then place the device into the cervical opening with the finger.

These features and advantages of the present invention will become more fully apparent from the following description and appended claims, or may be learned by the practice of the invention as described below.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF THE INVENTION

Figure 1:
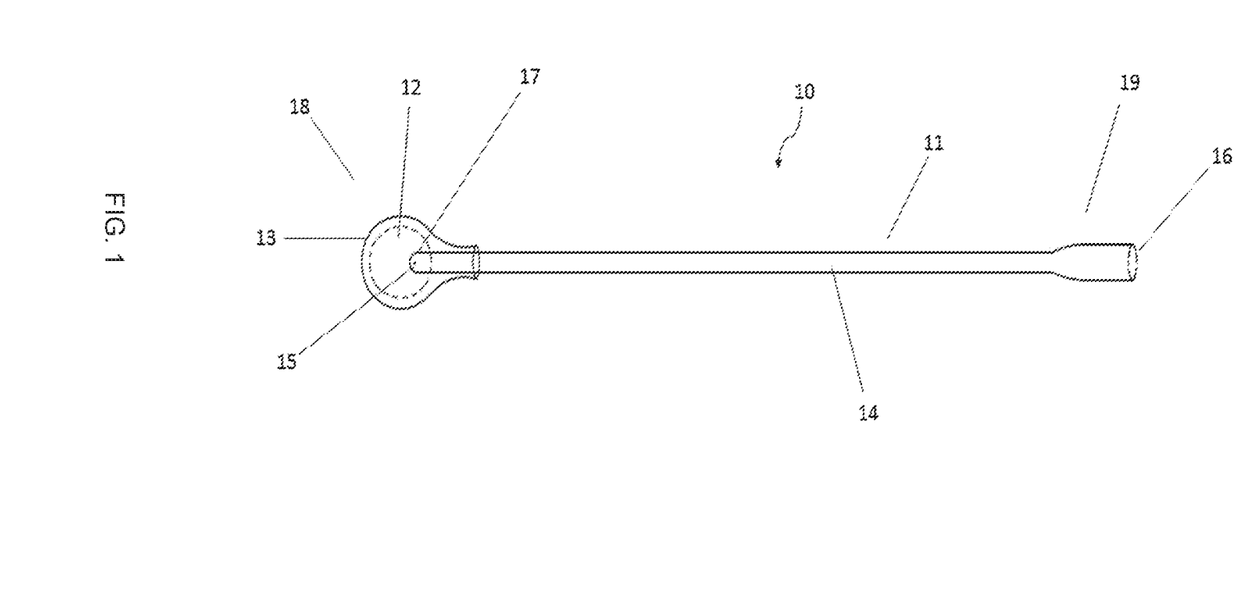
FIG. 1 illustrates a view of an embodiment of a cervical ripening device.

The present invention includes a system and methods for facilitating child birth that includes the use of a device that may be more easily positioned and inserted through the cervix to exert pressure on the internal os—through the inflation of a balloon—to facilitate cervical ripening. FIG. 1 illustrates one preferred embodiment of the invention. The system 10 comprises an elongated body 11, an inlet 16 at the proximal end 19, at least one balloon 12 disposed at the tip 17 of the distal end 18, an opening 15 at the distal end 18, an expandable member 13 adjacent to the balloon 12, and at least one lumen 14 disposed within the elongated body 11.

The elongated body 11 may be constructed of a flexible material such as silicone, rubber (e.g. nitrile rubber, styrene butadiene rubber, or butyl rubber), nylon, polyurethane, polyethylene terephthalate (PET), latex, thermoplastic elastomers, fluoropolymers, silicon, or other pliable materials known in the art. In certain preferred embodiments, the elongated body 11 may be constructed of silicon, and/or rubber materials that may allow the elongated body to flex and turn inside the vagina and cervix without causing unnecessary discomfort to the patient.

In preferred embodiments of the invention, the diameter of the elongated body 11 may be about 2.0 mm to about 6 mm, and more preferably about 2.5 mm to 3 mm. In further embodiments, the elongated body 11 may be about 10 cm to about 60 cm, about 10 cm to about 50 cm, about 10 cm to about 40 cm, about 10 cm to about 30 cm, about 10 cm to about 20 cm, or about 10 cm to about 15 cm in length. In other embodiments, the elongated body may be about 30 cm to about 40 cm in length. For purposes of this Application, the term "about" refers to an approximately +/−10% variation from a given value. It is to be understood that such a variation is always included in any given value provided herein, whether or not it is specifically referred to, unless stated otherwise. In still further embodiments, the length of the elongated body 11 may be less than 10 cm.

In other embodiments of the invention, the elongated body 11 may comprise one or more elongated body sections removably attached to one another by way of a fastening device, termed, for purposed of this application, a "removable section". Preferably, one removable section may be slightly greater in length than the total vaginal length—termed the "initial removable section"—such that a portion or end of the initial removable section protrudes from the vagina. At least a second removable section may be of similar, or greater length than the initial removable section, and may be removably attached to the initial removable section.

Attachment of the removable sections may be achieved through a fastening device such as, but not limited to, a pin, screw, locking tabs, clamps, or another locking device. In some embodiments, one or more ends of the removable section may have a screw locking device with internal or external threads that engage a complimentary thread pattern on a corresponding end of a second removable section. Twisting or other manipulation of the screw locking device engages the threads, thereby reversibly locking together each of the removable sections.

In one certain embodiment of the invention, one removable section may have an end with an outer diameter less than the inner diameter of an end of a second removable section such that the complimentary ends may nest within each other. Once the ends are joined together, a screw locking device or other fastening means may secure the removable sections in place. Using such methods, embodiments of the cervical ripening device may be constructed of any desired length.

Such adjustable devices may be useful, for example, when patients need to walk while the device is already positioned in the cervix. Prior to walking, the removable sections outside the vagina may be removed, leaving in place only the short initial section within the vagina. This may eliminate the physically uncomfortable, and potentially dangerous situation where the entire elongated body hangs freely out of the vagina.

Upon returning from the walk, the previously removed removable sections may be re-attached. The now full length elongated body may be further fixed to the patient's leg, the labor/delivery bed, or other locations to exert traction on the balloon to aid in cervical dilation.

Embodiments of the invention may include an inflatable balloon 12. The balloon 12 may have an expandable internal volume that may be filled to about 50 cc to about 100 cc, about 60 cc to about 90 cc, about 70 cc to about 80 cc, or about 75 cc to about 80 cc with fluid to exert sufficient pressure on the internal os upon inflation to facilitate cervical ripening.

In other preferred embodiments of the invention, the balloon 12 may be spherical or oblong in shape, and include one or more chambers (e.g. single chamber balloon, dual-chamber balloon etc.) The balloon 12 may be formed of a flexible material, such as polyurethane, and may have folds formed as a result of wrapping the balloon 12 around the elongated body 11 to facilitate insertion of the device into the cervix.

The balloon 12 may be inserted into the patient in an unexpanded state, and finable with fluid to produce an internal balloon volume. The balloon 12 may range from about 0.3 cm to about 0.5 cm in diameter in an unexpanded state and inflatable to about 1 cm to about 6 cm, or to about 3 cm to 6 cm, or more preferably, to about 5 cm to 6 cm. Preferably, the balloon has a narrow pre-inflation diameter to assist in insertion through the cervix into the internal os. Upon inflation, the balloon may expand to a certain diameter—dependent on the amount of pressure needed—to stimulate cervical ripening.

The elongated body 11 may contain at least one lumen 14, and, more preferably, at least two lumens disposed within the elongated body. However, certain embodiments may contain a plurality of lumens (e.g. 3, 4, 5 or more internal lumens). A lumen 14 may extend the length of the elongated body and may be open at one or both of the distal 18 and proximal ends 19 of the elongated body 11. The lumens may be used to transport fluid to and from the balloon 12 as necessary for inflation or deflation of the balloon, respectively.

Additional preferred embodiments of the invention may further include an expandable member 13. The expandable member 13 may be configured to receive the finger of a user, which may allow the user to place the device more precisely in the cervical opening. Preferably, the expendable member 13 may be at least partially attached to the elongated body 11, and at least partially covers or encloses the balloon 12.

The expandable member 13 may be about 1 cm to about 3 cm in length and about 0.3 to about 1.5 cm in diameter. In one preferred embodiment of the invention, the expandable member 13 may have a base diameter that may taper to a point or tip, mimicking the shape of a human finger. In another preferred embodiment, the expandable member 13 may be cone-shaped.

The expandable member 13 may be constructed of a biocompatible material such as latex, Polytetrafluoroethylene or polyethylene-like material, and may have a uniform thickness of about 1 mm, and preferably less than 1 mm to allow the user to easily feel the cervix.

The expandable member 13 and the balloon 12 may be positioned in close proximity to one another. For example, the balloon 12 may be located at the very tip 17 of the elongated body 11, or up to 5 mm from the tip 17, and the expandable member 13 positioned adjacent the balloon 12. The placement of the balloon at the tip, or near the tip of the device allows the user to insert only the minimal length of the device through the cervix to allow inflation of the balloon in the internal os.

In another preferred embodiment, the expandable member 13 may be positioned to cover the balloon 12, and, upon expansion, the material of the expandable member 13 may serve as an outer cover to the balloon 12. Such preferred embodiments may be used in situations where the cervix is minimally dilated and can accommodate only the finger diameter.

In some preferred embodiments, the expandable member 13 may be attached to the elongated body 11 proximal to the balloon 12 and encases, but is not directly attached, to the balloon 12. In this configuration, the balloon 12 may be free to expand within the expandable member 13 as the finger is slowly removed.

In another preferred embodiment, the balloon 12 may be positioned along the outside of, and in contact with the expandable member 13 with the balloon 12 located at the apex of the tip of the elongated body 11, or within about 5 mm from the tip 17. The balloon 12 may further be at least partially secured to the expandable member 13 so that it moves easily in response to finger manipulations.

In other preferred embodiments, the expandable member 13 may be directly attached to the elongated body 11 adjacent to the balloon 12. Preferably, the expandable member 13 may be attached to the elongated body 11 distally to the balloon 12. The expandable member 13 may extend over and cover the balloon 12 and tip 17. That is to say, the balloon 12 and tip 17 may be housed within the expandable member 13, but may not be directly attached to the expandable member 13 itself. This arrangement may cause the balloon 12 to be pulled tightly against the finger in use, essentially allowing the balloon 12 to move as an extension of the finger. Once the finger is in the correct position, the balloon 12 may be inflated, and the finger slowly withdrawn so that the balloon 12 and expandable member 13 remain in place to affect the cervical ripening.

Figure 2:
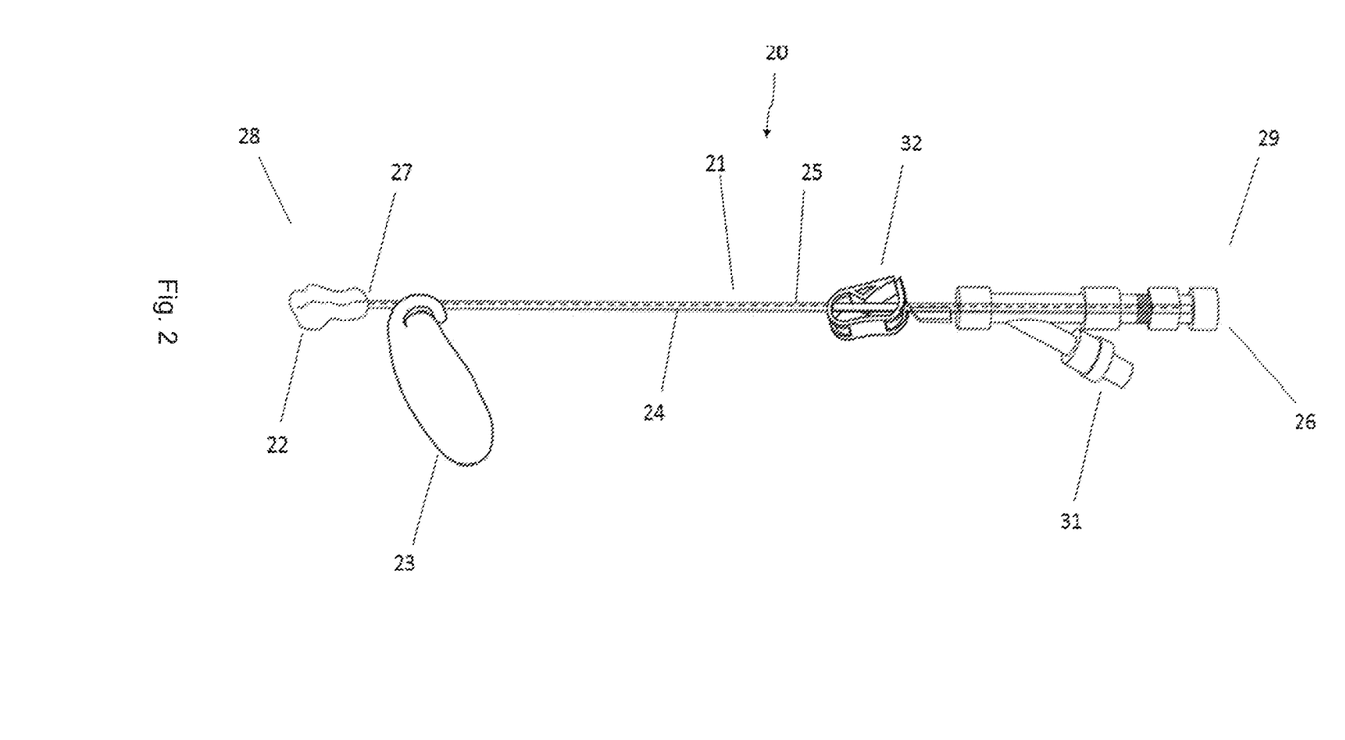
FIG. 2 illustrates a view of an alternate embodiment of a cervical ripening device.
Figure 3:
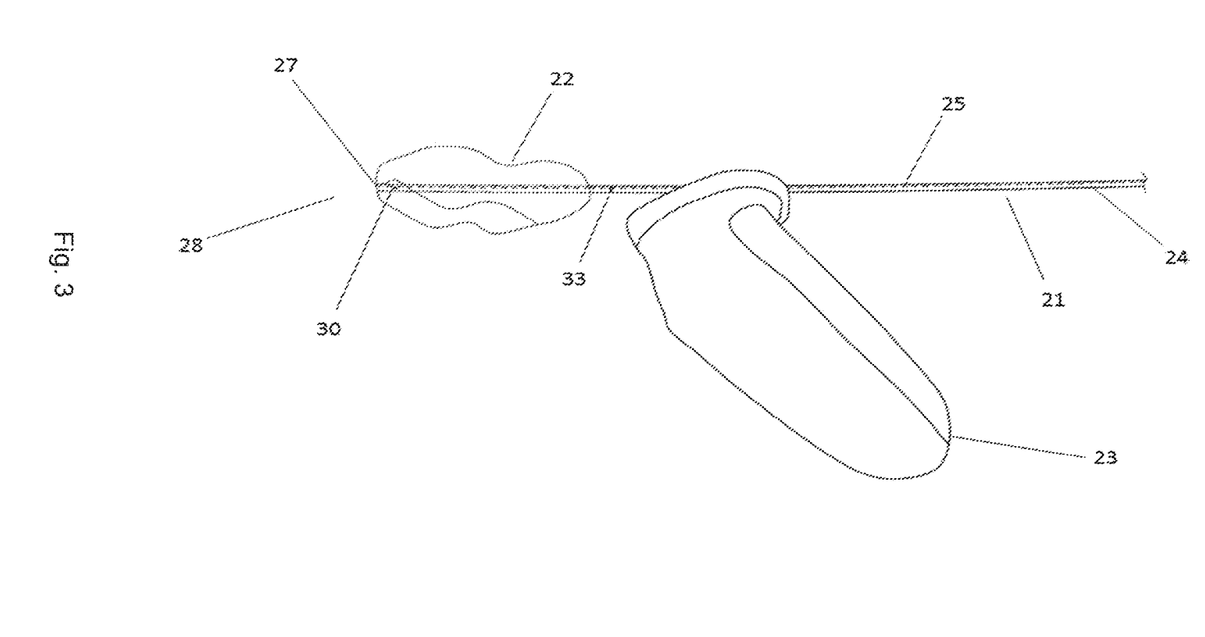
FIG. 3 illustrates a view of a distal end of an alternate embodiment of a cervical ripening device.

FIG. 2 and FIG. 3 disclose an alternate preferred embodiment of the invention. The system 20 comprises an elongated body 21, an inlet 26 at the proximal end 29, at least one balloon 22 disposed at the tip 27 of the distal end 28, an opening 30 at the distal end 28, an expandable member 23 adjacent to the balloon 22 and at least partially attached to the elongated body 21 (the expandable member 23 is shown rolled back to expose the underlying balloon 22 and tip 17), a main lumen 24 and a secondary lumen 25 disposed within the elongated body 21, and each lumen extending the length of the catheter. The elongated body may also include an injection port and valve 31 operably connected to one or both of the main lumen 24 or secondary lumen 25.

As shown in FIG. 2, certain preferred embodiments of the present invention may have at least one balloon 22 positioned at or adjacent to the tip 27 of the elongated body 21. In further embodiments, the balloon 22 may be positioned within about 5 mm of the tip 17. The expandable member 23 may be at least partially attached to the elongated body 21 at a position distal to the balloon 22, and may be rolled back from the tip to expose the balloon 22 or tip 27 as needed.

Embodiments of the invention may also include an injection port 35 and valve 31. The valve 31 may include any suitable valve, such as a ball valve, a needle valve, a flapper-style valve, a one-way valve, a two-way valve, or an inline rotary valve. The injection port 35 and valve 31 may also include, for example, an external device such as a syringe, a pump, an intravenous ("IV") bag, or another device to facilitate inflation and/or deflation of the balloon 22. Optionally, embodiment of the cervical ripening device may also include a stopper 32 to help control the flow of fluid through the device.

FIG. 3 illustrates the distal end 28 of an embodiment of the invention. The expandable member 23 is shown pulled back and retracted from tip 27 and balloon 22. A portion of the expandable member 23 may be attached to the elongated body 21. The balloon 22 may be connected at or near the tip 27. The balloon 22 covers an opening 30 that is in fluid communication with one or more internal lumens 24, 25.

Figure 4:
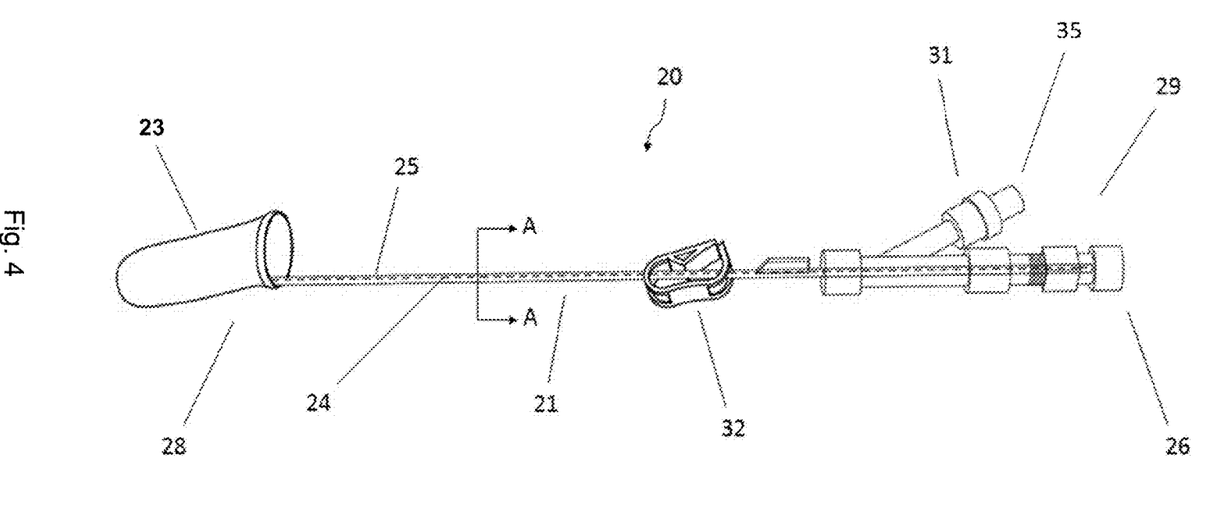
FIG. 4 illustrates a view of an embodiment of a cervical ripening device.

FIG. 4 illustrates the expandable member 23 positioned to cover the balloon 22 and tip 27 prior to use in a cervical ripening procedure. The expandable member 23 may completely cover the tip 27 and balloon 22. As shown, the expandable member 23, while covering the tip 27 and balloon 22, retains enough internal volume to further accommodate a user's finger for placement of the device into the internal os.

Figure 5:
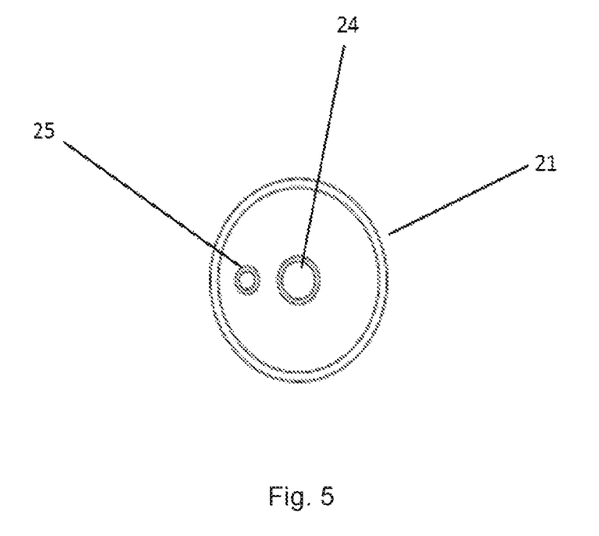
FIG. 5 illustrates a cross sectional view of the embodiment of a cervical ripening device shown in FIG. 4 along the axis A-A.

FIG. 5 illustrates a cross-section of the embodiment of FIG. 4, as viewed down the A-A axis, showing the elongated body 21, a main lumen 24, and a secondary lumen 25. Either the main lumen 24 or secondary lumen 25 may be used for inflation and deflation of the expandable balloon 22. For example, the main lumen 24 or secondary lumen 25 may extend from a fluid injection port 35 and valve 31 to the balloon, and allow the balloon—positioned to cover an opening 30 at the distal end of the lumen through which fluid may enter and leave the balloon 22—to affect inflation and/or deflation.

Figure 6:
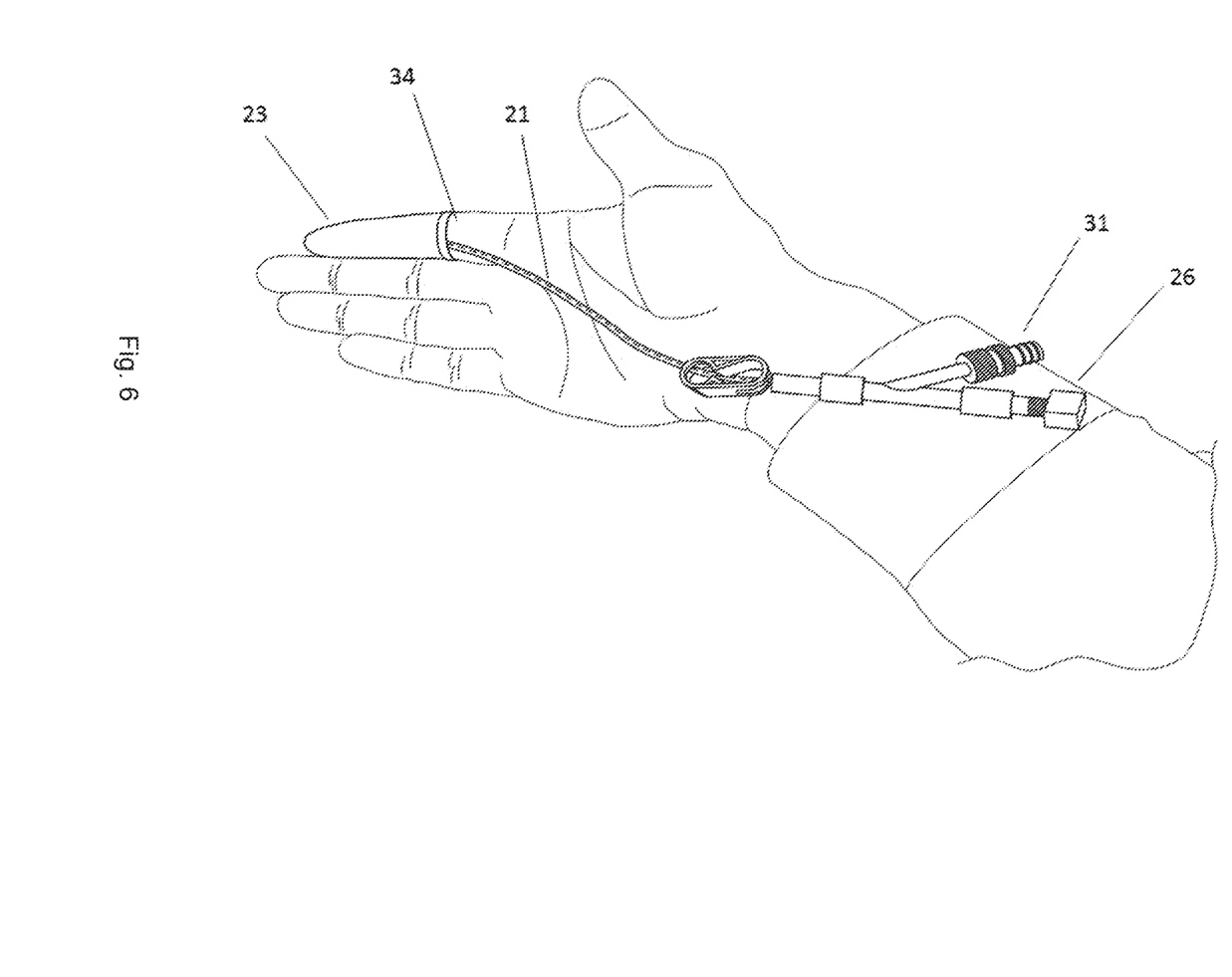
FIG. 6 illustrates the use of an embodiment of a cervical ripening device.
Figure 7:
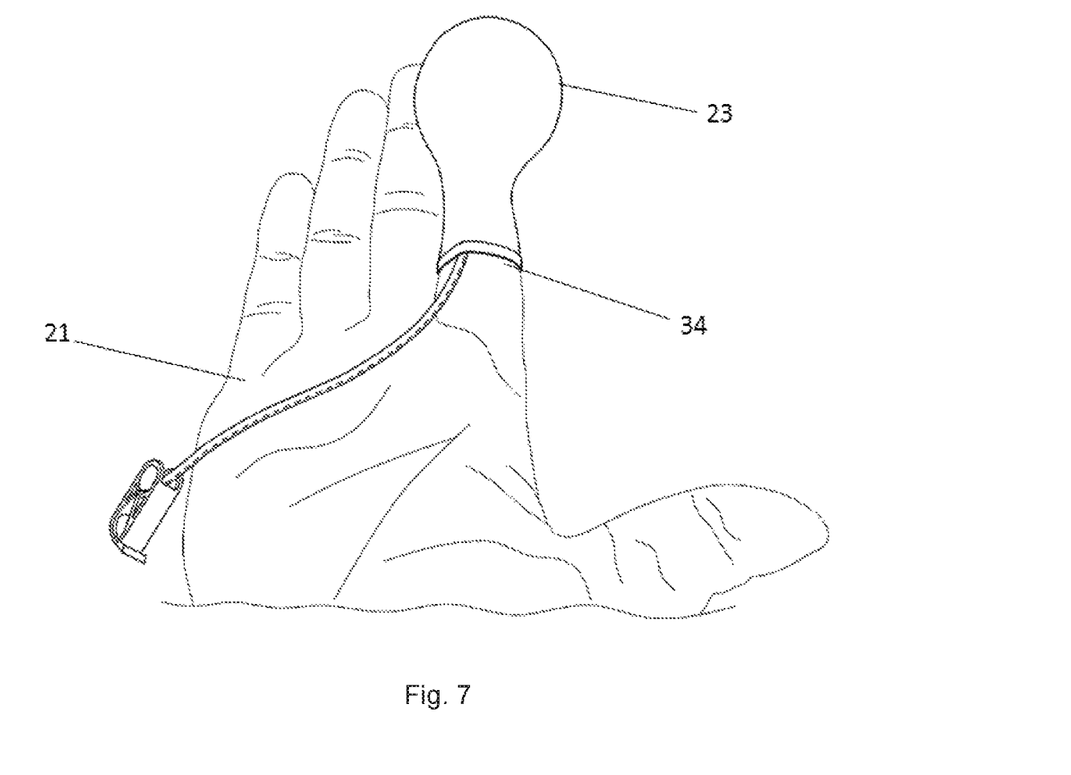
FIG. 7 illustrates the use of an embodiment of a cervical ripening device of the invention.

FIG. 6 and FIG. 7 illustrate an embodiment of the invention positioned on the finger of a user for use in a cervical ripening procedure. In FIG. 6, the expandable member 23—covering the balloon in the uninflated state (not shown)—may be configured to receive and accommodate the user's finger, and allows the user to easily place the finger in the device through the cervical canal using tactile manipulations. FIG. 7 depicts the device as it would be positioned at the internal os. Injection of a liquid through the injection port 35 and valve 31 may inflate the balloon with the finger still positioned inside the expandable member 23.

Optionally, embodiments of the invention may also include a semi-rigid, or rigid stylet. The stylet, for example, may be composed of plastic or plastic over a malleable or flexible metal core. The diameter of the stylet may be less than the diameter of the catheter, and more preferably, less than the diameter of at least one internal lumen, allowing for ease of stylet insertion and removal. Preferably, the distal end of the stylet is cushioned and devoid of metal, or includes a tab to prevent movement of the stylet to the tip 27, to prevent possible injury to the fetus, or rupturing of the balloon. Other embodiments of the invention may contain a stop or block 33 disposed in the main lumen 24 near the distal end 28 of the elongated body 23 to prevent travel of the stylet to the tip 27.

In other embodiments of the invention, the expandable member 23 may be removable from the elongated body 21 to aid in insertion when using an instrument such as a speculum.

In one certain preferred method of the invention, cervical ripening may be accomplished by inserting a finger into the expandable member of an embodiment of a device and placing the device within the vagina. Using tactile manipulations, the user may position the device at, and then past the cervical canal of the subject. Once in place, a fluid (e.g. air, water, saline, etc.) may then be injected through a lumen operably connected to an injection port to inflate the balloon and cause pressure to be exerted by the inflated balloon on the internal os. The finger may be removed from the device after inflation of the balloon, and the device held in place by the cervix. Once the desired level of cervical ripening is achieved, the balloon may be deflated by removal of the fluid through a lumen, and the device removed from the patient.

Further modifications and alternative embodiments of various aspects of the invention will be apparent to those skilled in the art in view of this description. Accordingly, this description is to be construed as illustrative only for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A device to facilitate child birth through cervical ripening comprising:
    an elongated body having a proximal end and a distal end;
    at least one lumen disposed within said elongated body;
    said distal end terminating in a tip at a distal end of the device, said tip being at least partially covered by an inflatable balloon disposed at said tip, the balloon being in fluid communication with the lumen to transport fluid to and from the balloon; and
    an expandable member disposed adjacent to said balloon and at least partially covering said inflatable balloon, wherein said expandable member, when expanded, accommodates a finger of a user to guide the distal end of the device for placement in an internal os to allow said inflatable balloon to expand and apply pressure to said internal os to facilitate the cervical ripening and the child birth.

2. The device of claim 1, wherein said elongated body is formed from an elastomeric polymer or silicone.

3. The device of claim 1, wherein said inflatable balloon is sized and shaped to expand to a balloon internal volume in order to accommodate about 80 cc of fluid.

4. The device of claim 1, wherein the at least one lumen comprises a main lumen and a secondary lumen, wherein a diameter of the main lumen is greater than a diameter of the secondary lumen.

5. The device of claim 1, wherein upon expansion, said expandable member is tapered from a narrow distal end to a broader proximal end.

6. The device of claim 1, wherein said expandable member is at least partially attached to said inflatable balloon.

7. The device of claim 1, wherein said expandable member is at least partially attached to said elongated body.

8. The device of claim 1, wherein said tip is positioned at least partially within said expandable member.

9. The device of claim 1, wherein the diameter of said elongated body is about 2.5 mm to about 3 mm.

10. The device of claim 1, wherein said elongated body is about 30 cm to about 40 cm in length.

11. The device of claim 1, further comprising a chamber operably attached to the proximal end of said elongated body and fluidly connected to the at least one lumen.

12. The device of claim 11, wherein said inflatable balloon is inflatable with fluid injected through the at least one lumen and, upon deflation of said inflatable balloon, the fluid is removed through the at least one lumen.

13. The device of claim 1, wherein said expandable member covers at least a portion of said inflatable balloon after expansion of said balloon.

14. The device of claim 1, wherein said expandable member completely covers said inflatable balloon after expansion of said inflatable balloon.

15. The device of claim 1, wherein said expandable member encases said inflatable balloon, the inflatable balloon being expandable within the expandable member.

16. A device to facilitate child birth through cervical ripening comprising:
an elongated body having a proximal end and a distal end;
one or more lumens disposed within said elongated body;
the distal end terminating in a tip at a distal end of the device, said tip being at least partially covered by an inflatable balloon disposed at said tip, the balloon being in fluid communication with the one or more lumens to transport fluid to and from the balloon;
an injection port disposed at the proximal end of said elongated body and operably connected to the one or more lumens; and
an expandable member at least partially attached to said elongated body and disposed adjacent to said balloon, said expandable member at least partially covering said inflatable balloon, and when expanded, said expandable member accommodates a finger of a user to guide the distal end of the device for placement in an internal os to allow said inflatable balloon to expand and apply pressure to said internal os to facilitate the cervical ripening and the child birth.

17. The device of claim 16, wherein said expandable member is at least partially attached to said elongated body distal to said inflatable balloon.

18. A device to facilitate child birth through cervical ripening comprising:
an elongated body having a proximal end and a distal end;
at least one lumen disposed within said elongated body, the at least one lumen comprising a main lumen and a secondary lumen, wherein a diameter of the main lumen is greater than a diameter of the secondary lumen;
said distal end terminating in a tip at a distal end of the device, said tip being at least partially covered by an inflatable balloon disposed at said tip, the balloon being in fluid communication with the lumen to transport fluid to and from the device; and
an expandable member disposed adjacent to said balloon and at least partially covering said inflatable balloon, wherein said expandable member, when expanded, accommodates a finger of a user to guide the distal end of the device for placement in an internal os to allow said inflatable balloon to expand and apply pressure to said internal os to facilitate the cervical ripening and the child birth.

19. A method for facilitating child birth through the use of a device that facilities cervical ripening, the method comprising:
placing a finger into an expandable member of a device according to claim 1 to cause expansion of said expandable member;
inserting a distal end of said device into a birth canal;
positioning, with a finger, said distal end of said device into an internal os; and
at least partially inflating a balloon to apply pressure to said internal os to facilitate the cervical ripening and the child birth.

* * * * *